United States Patent [19]

Olson

[11] Patent Number: 5,475,219

[45] Date of Patent: Dec. 12, 1995

[54] VALIDATION OF PHOTON EMISSION BASED SIGNALS USING AN ENERGY WINDOW NETWORK IN CONJUNCTION WITH A FUNDAMENTAL MODE DISCRIMINATOR CIRCUIT

[75] Inventor: Karl W. Olson, Worthington, Ohio

[73] Assignee: Neoprobe Corporation, Dublin, Ohio

[21] Appl. No.: 329,505

[22] Filed: Oct. 26, 1994

[51] Int. Cl.[6] ............................. G01T 1/161; G01T 1/24
[52] U.S. Cl. .............................. 250/336.1; 250/370.06
[58] Field of Search .......................... 250/336.1, 369, 250/370.01, 370.13, 370.06

[56] References Cited

U.S. PATENT DOCUMENTS

| | | | |
|---|---|---|---|
| 4,801,803 | 1/1989 | Denen et al. | 250/370.01 X |
| 4,889,991 | 12/1989 | Ramsey et al. | 250/336.1 |
| 4,893,013 | 1/1990 | Denen et al. | 250/336.1 |

Primary Examiner—Carolyn E. Fields
Assistant Examiner—Edward J. Glick
Attorney, Agent, or Firm—Mueller and Smith

[57] ABSTRACT

A system for detecting photon emissions wherein a detector serves to derive electrical parameter signals having amplitudes corresponding with the detected energy of the photon emissions and other signal generating events. Two comparator networks are employed within an energy window defining function to develop an output, L, when an event based signal amplitude is equal to or above a threshold value, and to develop an output, H, when such signal amplitude additionally extends above an upper limit. Improved reliability and accuracy is achieved with a discriminator circuit which responds to these outputs L and H to derive an event output upon the occurrence of an output L in the absence of an output H. This discriminator circuit is an asynchronous, sequential, fundamental mode discriminator circuit with three stable states.

17 Claims, 8 Drawing Sheets

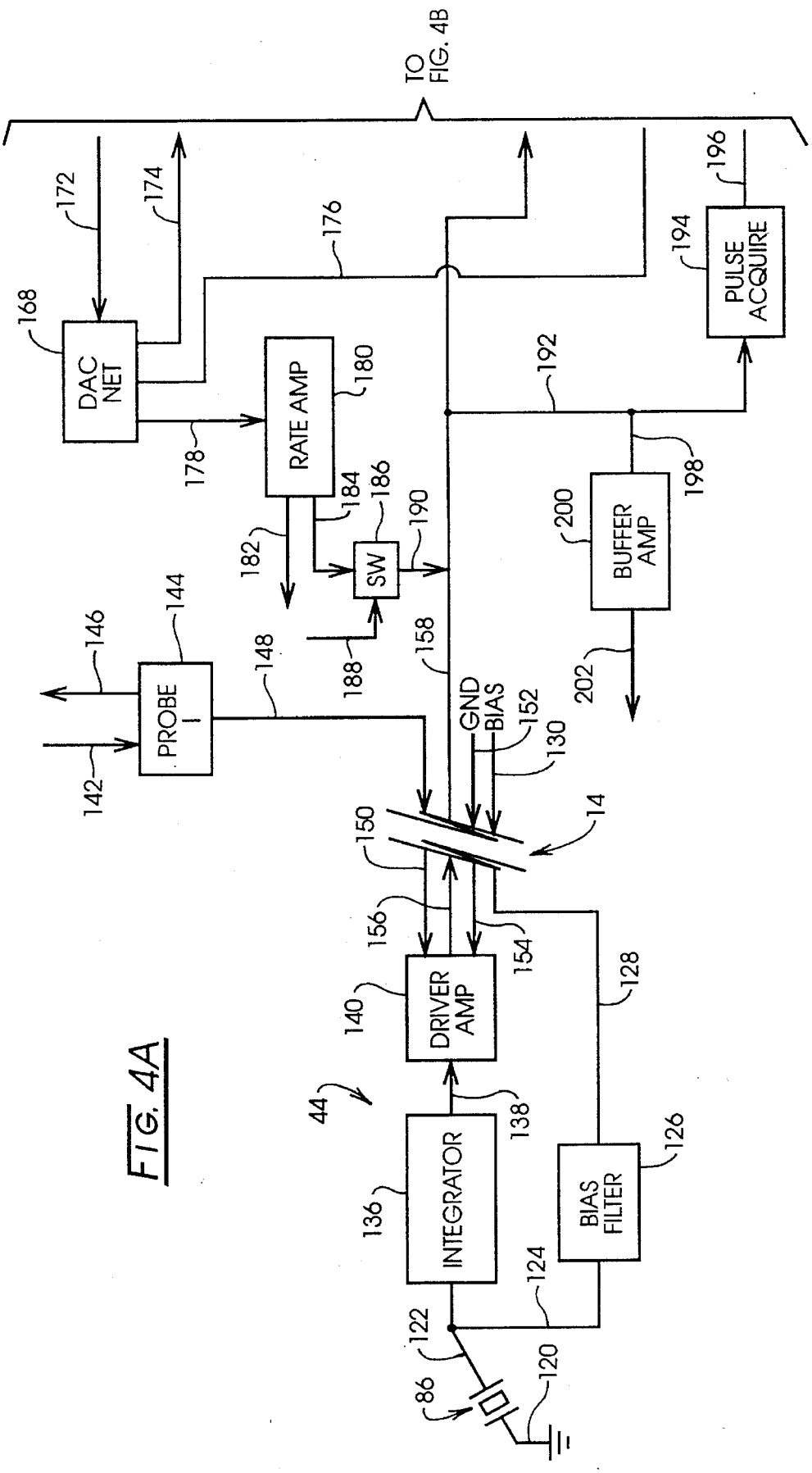

VALIDATION OF PHOTON EMISSION BASED SIGNALS USING AN ENERGY WINDOW NETWORK IN CONJUNCTION WITH A FUNDAMENTAL MODE DISCRIMINATOR CIRCUIT

BACKGROUND

Surgery has been the classic treatment modality for cancer, and until somewhat recently, was the only treatment offering a potential cure for patients. Such a surgical approach perhaps has been predominant in the treatment of colorectal cancer. Worldwide, the incidence rates of this form of cancer vary widely, from 3.4 cases per 100,000 population in Nigeria to 35.8 cases per 100,000 population in Connecticut. See generally:

*Cancer, Principles and Practice of Oncology*, vol. 1, 4th ed. p. 931, J. B. Lippincott Co., Philadelphia, Pa.

Where a surgical operation is elected for treatment, the resultant procedure is one of localizing the site of neoplastic tissue, or its biological precursor, differentiating it, and resecting it. ("Neoplastic tissue", for the present purposes, often is referred to as cancerous tissue, though malignant tumor and malignant tumor cells also are found in the terminology of the art. The term "neoplastic tissue" includes all of these as well as those biological disturbances occurring prior to tumor cell generation.)

The conventional practice of surgeons in locating and differentiating colorectal tumor has been through the senses of three-dimensional vision and touch, tissue under investigation being carefully observed for regions of tumor and palpated to locate that tumor which, for example, is not seen. Success in surgical procedure, however, requires that the surgeon locate all neoplastic tissue including the very smallest tumor. In fact, certain tumor, referred to as "occult" tumor, i.e. tumor which cannot be found by the conventional surgical procedures of sight and feel are somehow required to be located to assure success. Failure to locate and remove such occult tumor generally will result in the continued growth of cancer in the patient, a condition often referred to as "recurrent" cancer. This need to locate all neoplastic tissue has led to a variety of techniques to aid the surgeon. For example, a substantial amount of effort for aiding in the location neoplastic tissue has been through the utilization of radiolabeled antibody for detection purposes. One technique includes the scintillation scanning of patients injected with relatively high energy, e.g. $^{131}$I labeled antibodies. Such photo-scanning or scintillation scanning provides scintigrams difficult to interpret because of blood pool background radioactivity. Computer subtraction of radioactive blood pool agents and the use of two labeled antibodies (one specific for the tumor and one non-specific) have been attempted to enhance imaging. Nevertheless, such techniques have been found to provide little, if any, useful information to the surgeon, especially over and above CAT scans, magnetic resonance imaging, and like traditional techniques. Generally, these conventional imaging techniques will fail to locate occult tumor. As neoplastic tissue sites become smaller, the radionuclide concentrations will tend to be lost, from an imaging standpoint, in the background where blood pool radiation necessarily is present in the patient.

U.S. Pat. No. 4,782,840 by E. W. Martin, Jr., M.D., and M. O. Thurston, Ph.D. entitled "Method for Locating, Differentiating, and Removing Neoplasms", issued Nov. 8, 1988 (the disclosure of which is expressly incorporated herein by reference) reviews such scintillation scanning techniques and discloses a much improved method for locating, differentiating, and removing neoplasms. This procedure utilizes a radiolabeled antibody and a hand-held radiation detection probe which the surgeon may use intra-operatively in order to detect sites of radioactivity. The procedure is known as the "RIGS" system (RIGS being a trademark of Neoprobe Corporation, Columbus, Ohio) and is seen to achieve success in locating occult tumor. This is, in part, because the approach to localization recognizes that tumor detection should be delayed until the blood pool background of circulating radiolabeled antibody has had an opportunity to be cleared from the body. Fortuitously, the '840 patent discloses the ability of the radiolabeled antibody to remain bound to or associated with neoplastic tissue for extended periods of time with the radio tags still bound thereto. Moreover, even though the accretion of radioactivity at the tumor or neoplastic tissue site decreases over time, the blood pool background and surrounding tissue, relative to the tumor sites decreases at a much greater rate so that the radioactive sites can be determined utilizing a hand-held probe when it is positioned in close proximity with the tissue under investigation. Thus, the portable detection probe inherently employs the application of the approximate inverse square law of radiation propagation. Occult and otherwise unrecognizable neoplastic tissue is located because, for example, the number of rate based counts representing background radiation is very low, such that the resulting combination of background radiation plus the hint radiation emanating from neoplastic tissue will, while in and of itself remaining at a low level of count rates, will be detectable by a probe-contained radiation responsive crystal and its associated circuitry. To derive the presence or absence of such occult tumor, a microprocessor-driven complex system of analysis continuously works to statistically evaluate validated counts to aurally apprise the surgeon of the presence or absence of occult neoplastic tissue. The complex algorithm under which the noted evaluation takes place is described in U.S. Pat. No. 4,889,991 by R. C. Ramsey and M. O. Thurston, entitled "Gamma Radiation DetecTor with Enhanced Signal Treatment", issued Dec. 26, 1989 (the disclosure of which is expressly incorporated herein by reference). As is apparent, the data developed from the hand-held surgical probe must itself be accurately validated. This calls for amplification procedures which themselves are accurate and generally noise free; as well as photon event energy evaluations through the utilization of energy discriminating circuitry which is essentially free of inaccurate energy determinations with respect to asserted electrical signal pulses, the amplitudes of which correspond with photon emission energies.

Experience with the RIGS system has demonstrated its additional value in locating very hint neoplastic tissue occurring as a consequence of the commencement of metastasis. Not only is such neoplastic tissue located for resection, but also the surgeon is given a valuable aid in determining the proper staging of the patient in accordance with the extent and severity of the disease. Such staging aids in determining the appropriate post-surgical treatment for patients. Stage I and II patients are believed to be curable by surgery alone, whereas Stage III patients, i.e. patients determined to have cancer spread to the lymph nodes, are treated with some form of post-operative therapy, such as chemotherapy. Stage IV patients, i.e. patients with metastasis to other organs, are treated with a variety of methods, including post surgical therapy and/or surgical removal of tumor. Should hidden or occult neoplastic tissue not be found, residual disease is left behind and is not accounted for with respect to an evaluation of the extent of the disease.

The spread of colorectal cancer from its primary situs has been the subject of substantial study, the data from which can be more effectively used by the surgeon in conjunction with an understanding of the location of occult neoplastic tissue, i.e. a substantially improved evaluation of the extent of spread of the disease. Colorectal cancer first metastasizes to the perirectal nodes at the level of the primary tumor or immediately above it. Next, the chain accompanying the superior hemorrhoidal vessels is involved. In later stages of disease, when the hemorrhoidal lymphatics are blocked, there is lateral or downward spread. In colon carcinoma, normal lymphatic flow is through the lymphatic channels along the major arteries, with three eschilons of lymph nodes, pericolic, intermediate, and principal. If tumors lie between two major vascular pedicles, lymphatic flow may drain in either or both directions. If the central lymph nodes are blocked by tumor, lymphatic flow can become retrograde along the marginal arcades proximally and distally. The risk for lymph node metastasis increases with increasing tumor grade, as does the number of lymph nodes affected.

The liver is the primary site of hematogenous metastases, followed by the lung. Involvement of other sites in the absence of liver or lung involvement is rare.

Implantation refers to the release of tumor cells from the primary tumor and their deposition on another surface. Implantation has been reported with tumor cells shed intraluminally, from serosal surface through the peritoneum, and by surgical manipulation and resultant deposition on wound surfaces.

See generally:

"Second-Look Surgery for Colorectal Cancer, The Second Time Around" by Martin, et al., Ann. Surg. vol. 214, no. 3, pp 321–327, September, 1991.

"Manual for Staging Cancer" 4th Ed., edited by Beahrs, et al., pp 75–82, 1992, J. B. Lippincott Co., Philadelphia, Pa.

Because of the high sensitivity of the RIGS system, lymph node involvement and the like may be identified at very early stages of colorectal cancer metastasis. This sensitivity may be occasioned by a form of biological amplification occurring wherein the radiolabeling system serves to identify sialomucin, a substance secreted by cells experiencing preliminary cancer based disturbances as well as cancerous cells themselves. Thus, while precursors to tumor may be located, such identification is realized only with a capability for carrying out an accurate evaluation of very hint tumor associated photon emissions as combined with relatively low background level radiation.

To achieve higher levels of success in developing background versus tumor evaluation, the supporting instrumentation should exhibit very high levels of reliability. In this regard, noise based upon electronics must be limited or controlled, and the front end energy evaluations by discriminator networks must be as accurate as possible with an avoidance of hazards that may become present in logic networks to evoke inaccurate validations of photon emissions or events.

SUMMARY

The present invention is addressed to a system and apparatus for detecting photon emissions wherein a detector serves to derive electrical parameter signals having amplitudes corresponding with the detected energy of photon emissions and other signal generating events. Comparator networks are employed within an energy window defining function to develop an output, L, when an event based signal amplitude is equal to or above a threshold value, and to develop an output, H, when such signal amplitude additionally extends above an upper limit. Improved reliability and accuracy is achieved with a discriminator circuit which responds to these outputs L and H to derive an event output upon the occurrence of an output L in the absence of an output H. This discriminator feature is provided as an asynchronous, sequential, fundamental mode circuit with three stable states.

As another feature, the invention provides a system for detecting photon emissions, each occurring at an energy of interest within a range thereof. A detector assembly is provided having an input confronting the photon emissions and is responsive thereto to derive electrical parameter signals, each having an amplitude corresponding with the energy of interest. A first comparator network responds to each of the electrical parameter signals to have an output L when such signal exhibits an amplitude of value above a threshold value. A second comparator network responds to each electrical parameter signal and has an output H when the signal exhibits an amplitude of value above an upper limit value. An asynchronous, sequential, fundamental mode discriminator circuit is provided which is responsive to the output L and the output H, and has three stable states, a, b, and c, and has a no event output condition when in such a stable state. The discriminator circuit transitions from the state a to the state b upon the occurrence of an output, L, without the presence of the output H and transitions from the state b to the state a to derive an event output upon termination of the output L during state b without the presence of the output H. A control arrangement responds to each derived event output for effecting an evaluation thereof.

Other objects of the invention will, in part, be obvious and will, in part, appear hereinafter.

The invention, accordingly, comprises the system and apparatus possessing the construction, combination of elements, and arrangement of parts which are exemplified in the following detailed disclosure.

For a fuller understanding of the nature and objects of the-invention, reference should be had to the following detailed description taken in connection with the accompanying drawings.

BRIEF DESCRIPTION OF THE DRAWINGS

FIGS. 4A and 4B combine as labeled to form a block diagram of the functional components of the control system associated with the instrument and console of FIG. 1;

DETAILED DESCRIPTION OF THE INVENTION

The asynchronous, sequential, fundamental mode discriminator circuit employed with the system of the invention serves to provide energy window-based evaluation of signals representing photon emissions or events with a very high degree of reliability. This improved front-end signal treatment, in turn, results in more reliable statistical evaluations which are carried out to continuously evoke determinations as to the presence or absence of tag developed emissions over background noise.

Figure 1:
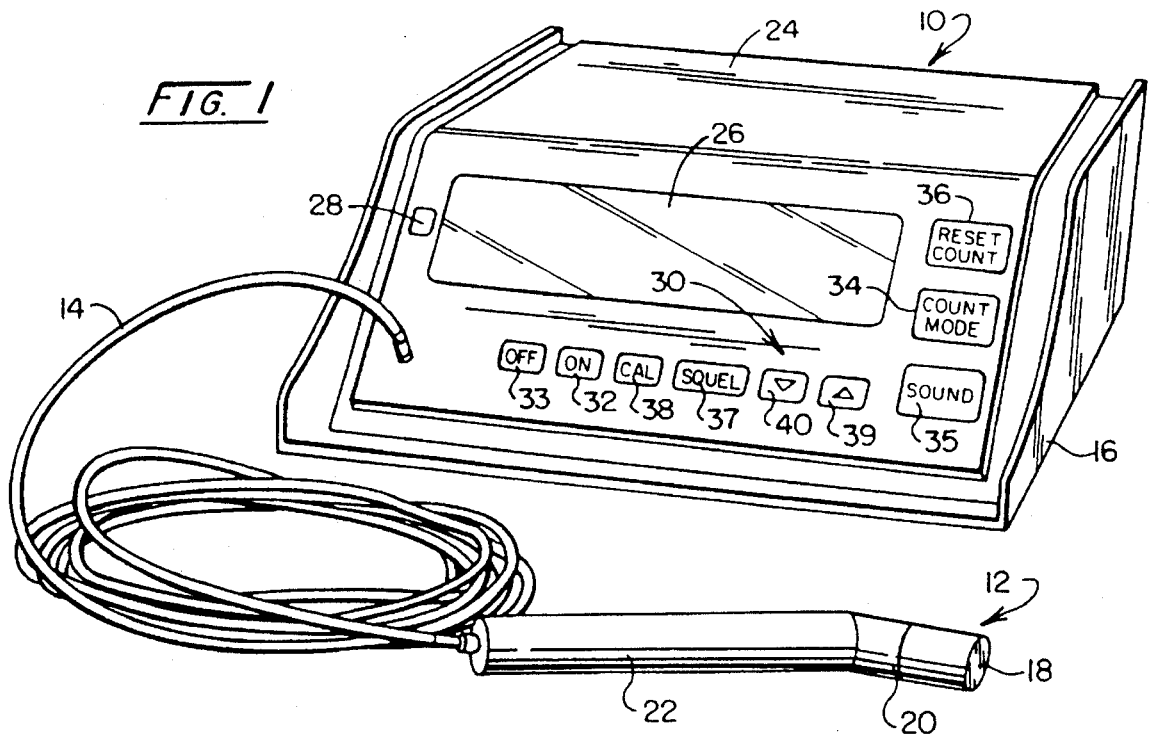
FIG. 1 is a perspective view of a probe instrument and associated console employed with the instant invention.

Referring to FIG. 1, an embodiment of the probe and supporting instrumentation with which the RIGS procedures are carried out is represented generally at 10. This assemblage includes a hand manipular probe represented generally at 12 which is coupled by a triaxial cable 14 to a console 16. The probe 12 is utilized following a preliminary procedure wherein the surgeon employs the classical techniques of visualization and palpation to locate larger tumor. Thus, the probe 12 is employed to carry out the function of locating occult neoplastic tissue. Generally, the device initially is positioned against a predetermined region of tissue for an interval, for example, of five seconds, whereupon background counts are evaluated and a mean value for background, $\overline{X}$ is automatically computed. Microprocessor driven algorithms then are carded out in accordance with user selections to establish or set a significance level above which the presence of neoplastic tissue reliably may be present. Generally, this is carded out by setting that level as three standard deviations above the background mean, $\overline{X}$, i.e. the level will be $\overline{X}+\overline{X}$. Thus, if a mean background level $\overline{X}$, is nine counts per second, the statistical significance level would require 18 counts per second to represent the presence of neoplastic tissue. These count levels being somewhat typical, it may be apparent that the quality of front end signal treatment for the system is quite important. Using the probe 12, the surgeon will move it along tissue of interest until, typically, a form of audible "chirp" is evoked as a consequence of a running statistical evaluation. The surgeon then will return to the location in tissue where the sound was heard and explore that region further. A technique generally utilized is to remain at that location for an interval of two seconds to confirm whether or not neoplastic tissue is present or whether an excursion in background had occurred. Thus, where the aural signal to the surgeon indicates the presence of tumor, the opportunity for a false designation is unlikely to the extent that for most applications, there will be less than a 1% probability that mere background is present at the location under investigation. The aural cue to the surgeon is generated from a loudspeaker or the like mounted within the console 10 and the program which generates this sound is referred to within the RIGS system as the "siren" form of output. Probe 12 is of a convenient length which is selected for comfort in grasping it, and is seen to include a radiation acceptance surface or window 18 utilized to confront the tissue under investigation. Window 18 is located at the tip of an angularly oriented portion 20 of the probe 12. Portion 20 extends from a hand grippable portion 22 at an angle of about 30° to facilitate its maneuverability about the back or hidden side of organs, To assure closeness to the source of photon emission, the window portion 18 will be positioned in direct contact with the tissue under investigation in most cases.

Typically, the probes 12 are gas sterilized for surgical procedures.

Because the assemblage 10 is used in a surgical theater, the console 16 is configured for cleaning, having a smooth, one-piece touch sensitive polymeric surface 24 surmounting a relatively large LCD readout or display 26, a dual colored LED readout 28, and a sequence of finger actuated switches. These switches or keyboard, as represented generally at 30 permit the microprocessor driven console 16 to carry out an instructive or "user friendly" dialogue with the practitioner. For purposes of safety, the device is powered by a rechargeable battery.

In addition to conventional on and off switches shown, respectively, at 32 and 33, the switches provided on console 16 include a count mode switch 34, a sound switch 35, a reset count switch 36, a statistical significance level selection switch referred to by the term "squelch" 37, a calibration switch 38, and up and down incrementing switches for adjustment within certain of the switch generated modes as shown, respectively, at 39 and 40.

Figure 2:
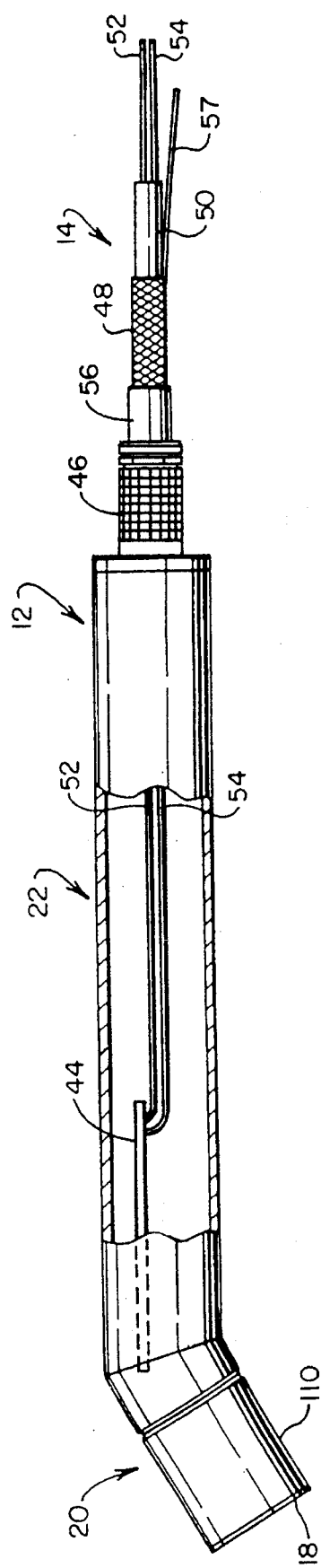
FIG. 2 is a side elevational view of the probe instrument shown in FIG. 1 with portions broken away to reveal internal structure.

Looking to FIG. 2, a more detailed representation of the probe device 12 is revealed. The angular orientation of the front portion 20 is shown having the noted 30° cant with respect to the central axis of the hand grip portion 22. Device 12 is somewhat small, having an overall length of about 19 cm and portion 22 having a length of about 12.7 cm. The overall diameter of the cylindrical structure 12 is about 1.9 cm. Because of the low count rates encountered by the device 12, it is desired to achieve as large a crystal confronting surface as possible as extending through the window 18 and, as is apparent, collimation or the like would not be used, and is specifically avoided for the application at hand. Hand grip portion 22 carries a preamplifier, typically on a forwardly disposed circuit board as represented in general at 44. Device 12 further is formed of a metal serving additionally as a shield against radiation.

Cable 14 supplies power to the preamplifier of the probe as well as bias and ground to the alloyed cadmium telluride crystal therein, and functions to transmit the electrical parameter signals generated by the detector assembly which includes a preamplification function. The cable 14 extends from a plug connector 46 and includes a braided shield 48 which extends over an insulating polytetrafluoroethylene (TEFLON) cover 50 which extends over three leads 52, 54, and 56. These leads, formed of TEFLON insulated silver, respectively, carry the output signals from the preamplifier at circuit board 44 and a bias signal for application to the rear face of the cadmium telluride crystal within device 12. Lead 56 carries a power supply for the preamplifier circuit. A drain wire 57 carries ground for the system and is coupled with the braided shield 48. An outer silicon rubber cover then is provided at 56.

Figure 3:
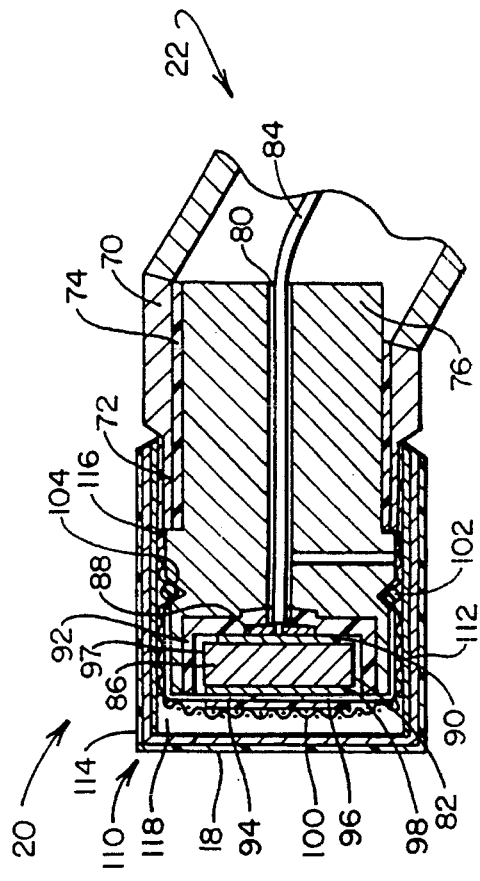
FIG. 3 is a sectional view of the forward portion of the probe instrument represented in FIG. 2.

Referring to FIG. 3, a component of the hand graspable portion 22 of the probe 12 is seen in section along with the angled portion 20. This sectional representation reveals the internal, crystal supporting components of the device. In this regard, the tubular portion 22 is connected to a supporting tubular portion 70 which extends forwardly to a cylindrical connector surface 72 of lesser outer diameter. The inwardly disposed cylindrical surfaces of support tubular portion 70 as well as connector surface 72 serve to receive and retain a generally cylindrically shaped slug or crystal mount 76. This mount 76 is formed of a suitable radiation attenuating material such as lead, and the rearward portion of it is configured for being slidably received within tubular portion 70. Slug 76 is adhesively retained in the position shown through the utilization of a layer of electrically conductive epoxy cement 74. Extending centrally through slug 76 is an access opening 80 which extends forwardly for communication with a crystal receiving cavity represented generally at 82. Central opening 80 carries a Teflon insulated multi-strand lead 84 which serves to carry a bias signal as well as those charge signals generated from the crystal assembly. Positioned centrally within the cavity 82 is a cadmium telluride crystal 86 which is of generally cylindrical form and which is mounted in a cushion-like arrangement to avoid motion generated noise. This is because, in general, cadmium telluride forms of crystals may exhibit microphonic (piezoelectric) effects, and are very fragile. CdTe crystals may be alloyed and still are referred to as "cadmium telluride" or "CdTe" crystals for present purposes. A preferred cadmium telluride crystal as described in commonly assigned application Ser. No. 07/992,622, filed on Dec. 18, 1992 (and incorporated herein by reference), is CdTe material alloyed with zinc and generally represented by the expression: $Cd_{1-x}Zn_xTe$. In general, CdTe detecting crystals exhibit benefits such as operability at room temperature, high counting rates, and small size. The preferred $Cd_{1-x}Zn_xTe$ detector crystals for use in the present invention exhibit high stability with respect to noise generation when subjected to variations in temperature. Thus, these crystals are ideally suited for surgical procedures where calibration will occur at operating theater temperatures, i.e. about 15° C. and the probe devices will absorb the heat emanating from the body cavity of the patient undergoing surgery, a temperature excursion amounting, for example, to about 15° C. or 20° C. The proportioning of the Cd component and Zn component of the crystals may vary to provide an effective ratio selected to suit the particular requirements of the user. However, a lower limit or boundary for the proportion of zinc where x equals about 0.2 has been determined, while a correspondingly high boundary or limit wherein x equals 0.8 has been determined. The alloyed crystals are marketed by Aurora Technologies Corporation, San Diego, Calif., 92067. Additional information concerning the alloyed crystals is provided in the following publications:

Butler, Lingren, and Doty, "$Cd_{1-x}Zn_xTe$ Gamma Ray Detectors", IEEE Transactions on Nuclear Science, Santa Fe, N. Mex. 1991.

Butler, Doty, and Lingren, "Recent Developments in CdZnTe Gamma Ray Detector Technology", Proceedings of the International Symposium of the SPIE, Santa Fe, N. Mex., July 1992.

Doty, Butler, Schetzina and Bowers, "Properties of Cadmium Zinc Telluride Grown by a High Pressure Bridgman Method", J. Bac. Sci. Technol., vol. B10, June/July, 1992.

Returning to FIG. 3, the multiple strands of the insulated lead 84 as they extend forwardly through the opening 80 are spread apart and attached to an electrically conductive biasing contact member 88 which is generally thin and circularly shaped. Between this biasing contact member 88 and the rearwardly disposed surface of crystal 86 is an electrically conductive compliant member 90 of cylindrical shape. The member 90 may be formed, for example, of a non-woven TEFLON cloth containing carbon. This is a stretched, highly crystalline, unsintered polytetrafluoroethylene marketed under the trade designation "GORETEX" having a thickness, for example, of about 0.020 in. With this arrangement, bias can be asserted at the rearward face of crystal 86 without generation of metal to crystal induced noise. Extending about the periphery of cavity 82 is an in situ formed electrically insulative layer 92 over which the noted biasing contact member 88 and electrically conductive compliant member are positioned. This layer 92 extends along the side edges of the cavity 82 but is spaced from the sides of the crystal to define a gap therebetween, again in the interest of avoiding rubbing induced noise.

Ground is applied to the forward face of crystal 86 in conjunction with a compressive retention arrangement. In this regard, a grouping of fine platinum wires are mechanically and electrically coupled with the forward portion of slug 74 and extend over the forward face of crystal 86. Two of these wires are shown at 94 and 96. To prevent metal-to-crystal induced noise, another conductive and compliant member 98 is interposed between the wires and the forward surface of the crystal 86. Thus, ground is supplied through the wires, thence through the compliant member 98 and to the forward surface of crystal 86. The entire arrangement is retained in position in an overall compressive fashion by a resilient retainer 100 which is positioned in tension over the entire assembly and retained in such tension and position by a conventional elastic O-ring 102 which is located and retained within an annular group of generally V-shaped cross-section shown at 104. The resilient retainer may be provided as a web of nylon or the like. This web is positioned over the assemblage of components and drawn downwardly over them as well as over the outer surface of slug 76 to be retained by the noted O-ring 102.

A forward cover 110 is positioned over the above-described assemblage. This cover 110 is formed of a convenient radiation transmissive material such as aluminum. Utilization of such transmissive material for the entire cover is permissible inasmuch as the sides of the crystal retaining cavity of slug 74 block radiation from all directions except the forward face of crystal 86. Because the cover 110 functions as an electrical shield, the interior side surfaces thereof are made electrically conductive by the deposition thereon of a thin layer of gold as at 112. The coating functions to aid in avoiding friction generated noise occasioned by the movement of the device over tissue. The cover 110 is retained upon the cylindrical connector surface 72 by a conductive epoxy cement layer 116. Note in the figure that the assemblage of tubular portion 72, crystal 86, and cover 110 is such that upon final assembly, a dead space 118 is created between the forwardly disposed surface of crystal 86 and the window portion 18 of cover 110. This dead air space provides an enhancement of acoustic isolation of the crystal 86.

Figure 4B:
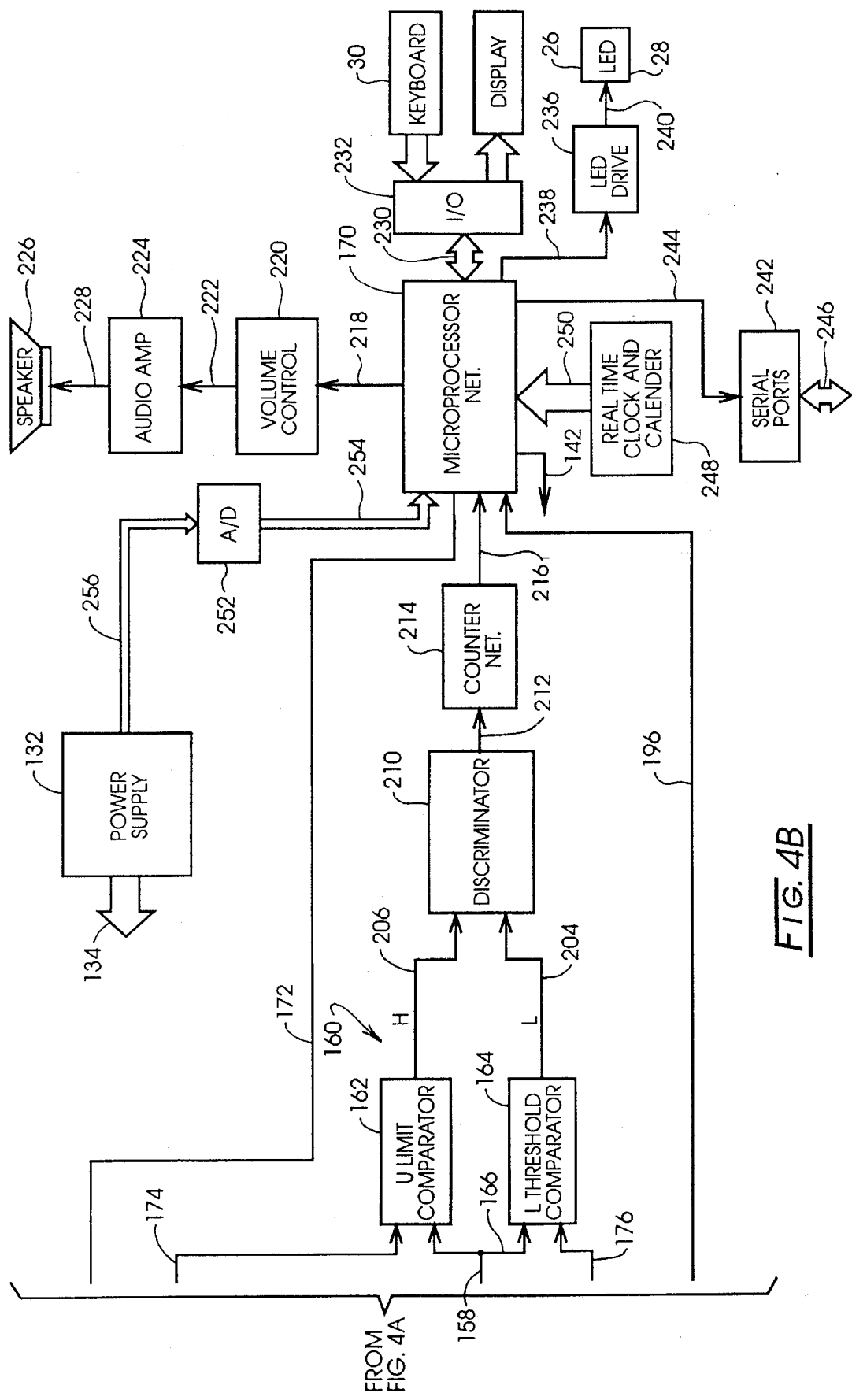

Referring to FIGS. 4A and 4B, a block diagrammatic representation of the circuitry supporting the probe 12 is portrayed. In FIG. 4A, the cadmium telluride crystal 86 is shown having one face coupled to ground through line 120, while the opposite, biased face thereof is coupled via lines 122 and 124 to a bias filter represented at block 126. The input to filter 126 is represented at line 128 as being applied through the cable as described earlier at 14 and represented by that numeral herein. Line 128 corresponds with earlier-described line 54. The bias input is seen to extend as represented at line 130 and emanate from a power supply shown in FIG. 4B at block 132, the various outputs of which are represented in general by the arrow 134. Line 122 from the crystal 86 is shown extending to an integrator stage 136 of the preamplification function 44. The integrated valuation of detected radiation disturbance then is shown directed as represented by line 138 to a driver amplification network shown at block 140. A preferred preamplification circuit for function 44 is described in a copending application for U.S. patent by Thurston, et al., Ser. No. 07/992,622, filed Dec. 18, 1992, entitled "Radiation Responsive Surgical Instrument" which is assigned in common herewith. A d.c. power supply is provided from the power supply represented at block 132 and at arrow 134, and is seen directed, as represented at line 142, to a probe current network represented at block 144. Under microcomputer control as represented at line 146, the network 144 develops signals, for example, determining whether the probe instrument 12 has been properly connected to the console 16. Delivery of the d.c. power supply for the preamplifier stage 44 is represented at lines 148 and 150. Ground to the probe 12 also is developed from the power supply at block 132 and arrow 134, as represented at lines 152 and 154. Line 154 corresponds, for example, with the earlier-described clad at 48 discussed in connection with FIG. 2, while line 50 corresponds with clad 46 of that figure.

The output of the preamplification function 44 is represented at lines 156 and 158, the former line corresponding with earlier-described line 54 (FIG. 2). Line 156 extends to line 158 which, in turn, extends to the input of an energy window network represented in FIG. 4B in general at 160. Looking additionally to FIG. 4B, it may be observed that energy window network 160 includes an upper limit comparator represented at block 162 as well as a lower threshold comparator represented at block 164. The photon event signals at line 158 which have been preamplified at function 44 are submitted simultaneously to each of these comparator functions 162 and 164 as represented at line 166. Correspondingly, the comparison values or limits associated with the upper limit comparator 162 are applied from a digital-to-analog converter (DAC) seen in FIG. 4A at block 168. In this regard, DAC 168 is under the control of a microprocessor network represented at block 170, such digital control to device 168 being asserted as represented at line 172. Thus, the upper limit asserted at comparator 162 is provided from DAC 168 as represented at line 174. Correspondingly, the lower threshold value for comparator function 164 is asserted from DAC 168 via line 176.

The microprocessor network 170, as represented by line 172 also develops an analog signal at DAC 168 as represented at line 178 which corresponds with the instantaneous pulse rate. This information is conveyed to a pulse rate amplifier network represented at block 180. The output of rate amplifier function 180 as represented at line 182 may be provided, for example, at the rear of console 16. The circuit represented at block 180 also may be employed to generate a calibrating pulse for testing the downstream components of the system. Thus, the microprocessor network 170 may apply a predetermined pulse level through the digital-to-analog conversion network 168 for presentation to the amplifier network represented at block 180. The resultant output at line 184 is selectively switched as represented at block 186 to provide a pulse width definition. In this regard, the switching function 186 is regulated as represented at line 188 from the microprocessor network 170, and the pulse categorized signal from switch 186 is introduced to line 158 as represented at line 190.

The signals at line 158 also are directed as represented at line 192 to a pulse acquire function represented at block 194. Network 194 functions, when activated by the microprocessor function 170, to acquire the value of the highest pulse amplitude witnessed at line 158. Periodically, this information then is transmitted to the microprocessor function 170 as represented by line 196. Representing a form of peak detector, the network 194 sometimes is referred to as a "snapshot circuit". Also produced from line 192 as at line 198 and block 200 is a buffer amplifier which will provide at line 202 an output representing received pulses which may be made available at the rearward portion of console 16 for conventional radiation evaluation purposes.

With the arrangement shown, the crystal detector assembly including cadmium telluride crystal 86 and associated preamplification network 44 derives electrial parameter signals in response to photon emissions which are confronted at crystal 86. Those electrical parameter signals will have an amplitude corresponding to the energy of interest of the photon emissions. Additionally, the signals may represent spurious phenomena such as cosmic rays and the like. Accordingly, the energy of the electrical parameters or amplitudes thereof are evaluated at the energy window network 160 seen in FIG. 4B. The lower threshold comparator function 164 will promulgate a pulse of fixed and consistent duration identified as "L" at line 204 when the signal asserted threat exhibits an amplitude of value equal to or above a threshold value. That threshold value is established, as noted above, from line 176. Correspondingly, the electrical parameter signals from line 158 will be evaluated by the upper limit comparator function 162 such that when the parameter signal exhibits amplitude of value above an upper libnit value established from line 174, a pulse of consistent and fixed duration identified as "H" will be promulgated at line 206. These outputs from lines 204 and 206 then are directed to the input of an asynchronous, sequential, fundamental mode discriminator circuit represented at block 210. Such circuits as at 210, while being sequential in nature, are not synchronized in any way with a clock signal. Of this circuit family, the fundamental mode form of circuits are defined as circuits with level inputs and unclocked memory elements. They are referred to, for example, as type 4 circuits as discussed, for example, in the publication: "An Introduction Computer Logic" by Nagle, Jr., et al., Prentice-Hall, Inc., Engelwood Cliffs, N.J. 1975. The discriminator function 210 serves to generate and event output in the form of finite pulse at line 212 upon the occurrence of an electrical parameter signal from line 158 which represents a photon emission which is valid from the standpoint of the energy range of interests associated with it. These pulses at line 212 then are counted by a counter function represented at block 214, whereupon, as represented at line 216, the count data is submitted to the microprocessor network 170 for statistical analysis as above discussed.

Microprocessor network 170 performs under a variety of operational modes to provide both audio and visual outputs to aid the surgeon in locating and differentiating neoplastic tissue. In the former regard, as represented at line 218 and block 220, a volume control function may be asserted under the control of microprocessor network 170. Generally, a "siren" type signal with frequency variation is asserted as represented at line 222 to an audio amplification circuit represented at block 224 for speaker 226 as represented at line 228. With the noted siren arrangement, the frequency output from speaker 226 increases with an exponential change from 20 Hz to 1200 Hz when the average count rate exceeds the preset significance or threshold level. Similarly, when an awrage count rate falls below the threshold, an opposite or frequency down output occurs. Network 170, as represented by arrow 230 and block 232, functions to provide a pulse count output of varying types as well as outputs representing volume levels, pulse height, noise levels, and battery status. Visual readout is represented in FIG. 4B as a block with the same display 26 numeration as described in conjunction with FIG. 1. Similarly, the input-output function represented at block 232 provides appropriate scanning of the keyboard or switches described in conjunction with FIG. 1 at 30 and represented by the same numeration in FIG. 4B. During a counting operation, the microprocessor network 170 functions to control a light emitting diode drive network represented by block 236 from line 238. The drive network represented at block 236 is shown providing an output, as represented by line 240, to the dual LED display as described at 28 in FIG. 1 and represented in block form with the same numeration. The readout provides a red light when a gamma ray is detected, and a green light during counting procedures in general. A serial output port of conventional variety also is provided on the console 16, such port being represented at block 242 as being addressed from the microprocessor function 170 from line 244 and having output and input components represented by the arrow 246. A real time clock-calendar having a non-volatile memory also may be provided in conjunction with the function of the microprocessor network 170 as represented by block 248 and arrow 250. Further, the microprocessor function 172 may be employed to monitor the performance of the power supply represented at block 132. This is shown being carried out by the interaction of the microprocessor network 170 with an analog-to-digital converter represented at block 252 and having an association represented by arrows 254 and 256. As is apparent, the converter 252 functions to digitize the analog values at the power supply 132 for submittal to network 170.

Figure 5:
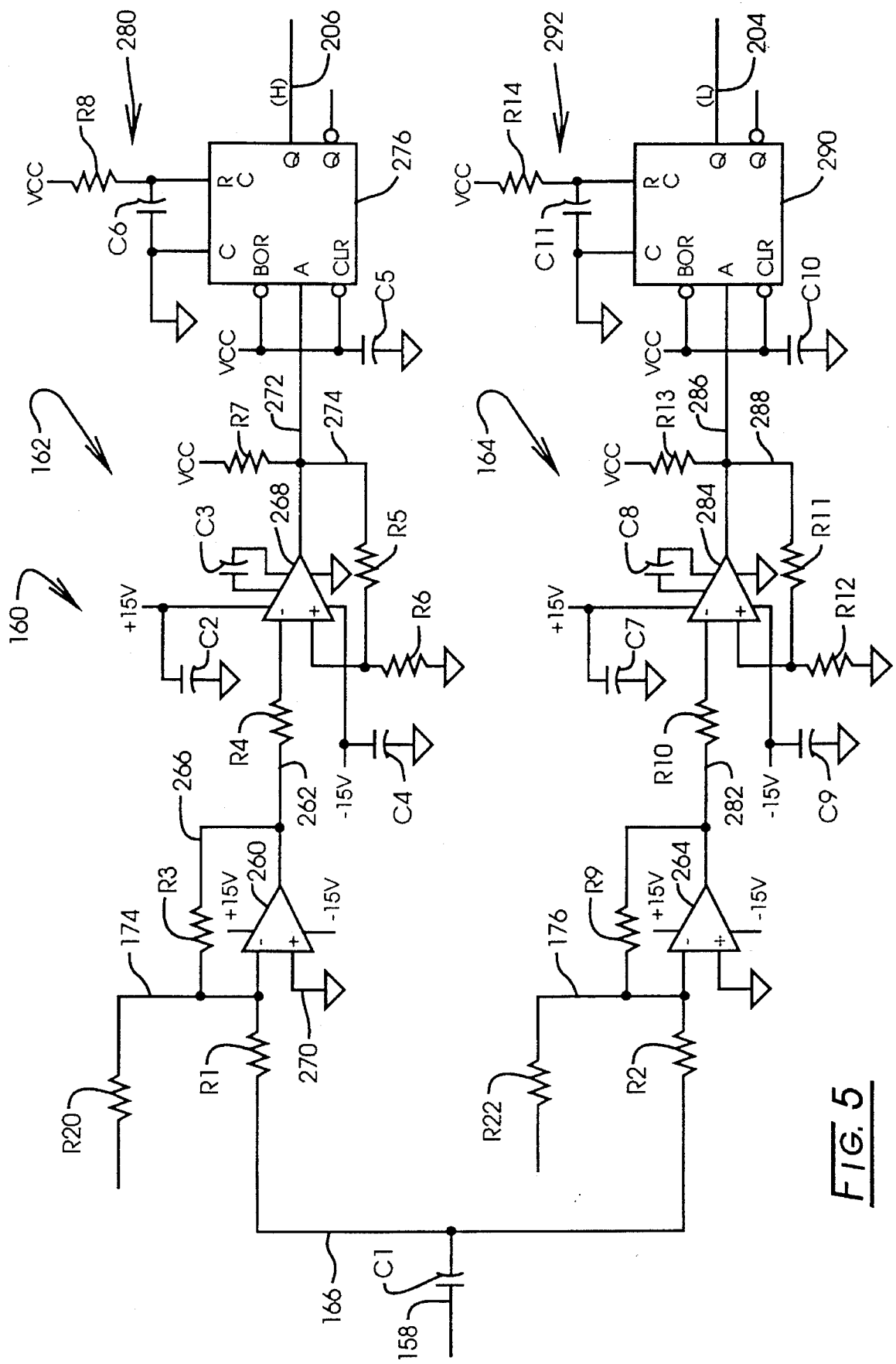
FIG. 5 is an electrical schematic diagram showing an energy window network employed with the instrumentation of FIG. 1.

Referring to FIG. 5, the energy window network described in general at 160 in connection with FIG. 4B is presented at an enhanced level of detail. Where appropriate, the same line identification from FIGS. 4A and 4B is retained. In this regard, note that line 158 carrying a preamplified signal occurs in conjunction with a blocking capacitor C1 and is directed to present preamplified signals and the like through line 166 simultaneously to the upper limit comparator circuit represented generally at 162 and lower threshold comparator circuit represented generally at 164. A preamplified signal at line 166 is directed through a resistor R1 to one input of an inverting stage operational amplifier 260 which is seen to be coupled to +15 v as well as −15 v and provides an output at line 262. The same signal from line 166 is directed via resistor R2 to the corresponding input of an inverting stage operational amplifier 264 of circuit 164. Devices 260 and 264 may be provided, for example, as type LF412 operational amplifiers. With the arrangement shown, the preamplified signal is evaluated with respect to the upper limit network 162 and the lower threshold network 164. The upper limit circuit 162 identifies spurious signals and the like which are represented by signal amplitudes greater than those of the radionuclide being employed. In similar fashion, the lower threshold network or circuit 164 functions to exclude those signals having energy amplitudes known to be below the radionuclide energies of interest, while identifying those having energy amplitudes above that same lower threshold. With the exception of the threshold and limit adjustment settings, the upper limit network 162 is configured identically with the lower threshold network 164. Looking initially to the upper limit network 162, adjustment for the upper threshold value is provided from along earlier-described line 174 emanating from the DAC 168 discussed in conjunction with FIG. 4A. Line 174 is seen to extend through resistor R20 to line 166 and the inverting input of stage 260. The output of stage 260 at line 262 incorporates a feedback resistor R3 within feedback path line 266. With the arrangement shown, the negative voltage at line 174 is summed in a weighted manner with voltage at the input to resistor R1. Thus, a gamma event preamplified pulse is presented at line 262 as a negative going waveform which is directed through resistor R4 to one input of a voltage comparator 268. Note that the non-inverting input to stage 260 is coupled via line 270 to ground.

Comparator 268 is configured with capacitors C2–C4 and is implemented with a regenerative feedback from its output line 272 incorporating resistors R5–R6 and path line 274. This arrangement provides a hysteresis form of performance to achieve a desirably defined pulse output corresponding with a gamma event. In this regard, the pulse output commences to be defined as the input voltage swings negative and then is fully defined when the input voltage returns to a predetermined positive level. Resistor R7 is a pull-up resistor coupled with VCC and line 272.

The output of comparator stage 268, in effect, derives a digital logic which must be clearly capable of interpreting a 0 or 1 logic level. To clearly demark whether or not a gamma event or non-event is at hand, the signal at line 272 is submitted to the A input of a monostable multi-vibrator 276 which is configured having a filtering capacitor C5 coupled with VCC input thereto and an RoC network 280 incorporating resistor R8 and capacitor C6. The resultant output at line 206 is quite well defined and of consistent width regardless of the width of the input at line 272. Line 206, as described in connection with FIG. 4B, is directed to one input of a discriminator 210. Device 276 may be provided as a type 74HC4538.

Looking to the lower threshold network 164, the output of inverting stage 264 is seen at line 282 and lower threshold adjustment is provided through resistor R2 from line 176 which, as described in connection with FIG. 4A, emanates from digital-to-analog converter 168 under the control of microprocessor network 170. A feedback path 548 extends about stage 264 which incorporates resistor R9 and the output at line 282 is a negative going one as is the case in connection with line 262 of stage or network 162. This output is directed through resistor R10 to one input of a comparator stage 284 having an output at line 286. Device 284 is structured identically with that at 268; is configured with capacitors C7–C9; and includes a regenerative feedback path including resistors R11 and R12, the path being designated at 288. A pull-up resistor R13 is coupled between output line 286 and VCC. As in the case of network 268, the pulse defined output at line 286 is directed to the A input terminal of a monostable multivibrator 290, the VCC input to which is filtered at capacitor C10 and which is configured with an R-C network 292 incorporating resistor R14 and capacitor C11. This arrangement, as in the case of network 162, provides a well defined pulse of consistent width at output line 204 which is directed to the lower window input of discriminator 210 (FIG. 4B). That pulse width is identical to the width of the pulse at line 206.

The discriminator device 210 as described in connection with FIG. 4B is one which validates the photon events by analyzing pulses of equal width presented at upper limit input line 206 and lower threshold input line 204. The circuit is a sequential circuit of a type referred to as "level asynchronous" which is one having level inputs and unclocked memory elements. As such, the circuit avoids the loss of count data as a consequence of spurious anomolies including hazards that may be confronted in the utilization of more typical circuits such as those responding to clock inputs utilized with pulsed synchronous circuits or level synchronous circuits. For the low count levels typically encountered with the RIGS surgical procedure in conjunction with very small neoplasm manifestations, the accuracies of the instant circuit are desirable.

In approaching the design of the circuit, criteria and assumptions initially are developed. In this regard, it is necessary that the discriminator process the output signals of the energy window network 160 and produce an output only when the peak preamplifier output voltage amplitude is greater than or equal to the lower threshold and less than the upper limit. In devising the circuit, assumptions are made, to wit:

the lower thresold and upper limit comparators as described in conjunction with FIG. 5 each exhibit hysteresis, however, this hysteresis does not affect the accuracy of the detection of the threshold or limit crossing since the regenerative feedback voltage of each comparator is zero when the input voltage is less than the threshold value;

a monostable multivibrator is connected to the output of each of the comparators for the purpose of reducing the probability of marginal outputs from the comparator function. The duration of the monostable multivibrator outputs, as for example at lines 204 and 206, is on the order of two gsec.;

the analog threshold levels for the upper limit and lower threshold comparators will normally be adjusted such that the upper limit is greater than the lower; however, the circuit is designed to function consistently when the upper limit is set to a value which is less than that for the lower threshold; and the output from the upper limit monostable multivibrator 276 will become active prior to the time-out of the lower threshold monostable multivibrator 290, this assuming that the voltage is great enough to exceed the limit value of the upper limit comparator network 162. The analysis to follow is one based upon a Mealy model wherein outputs are defined on a transition between states.

Figure 6A:
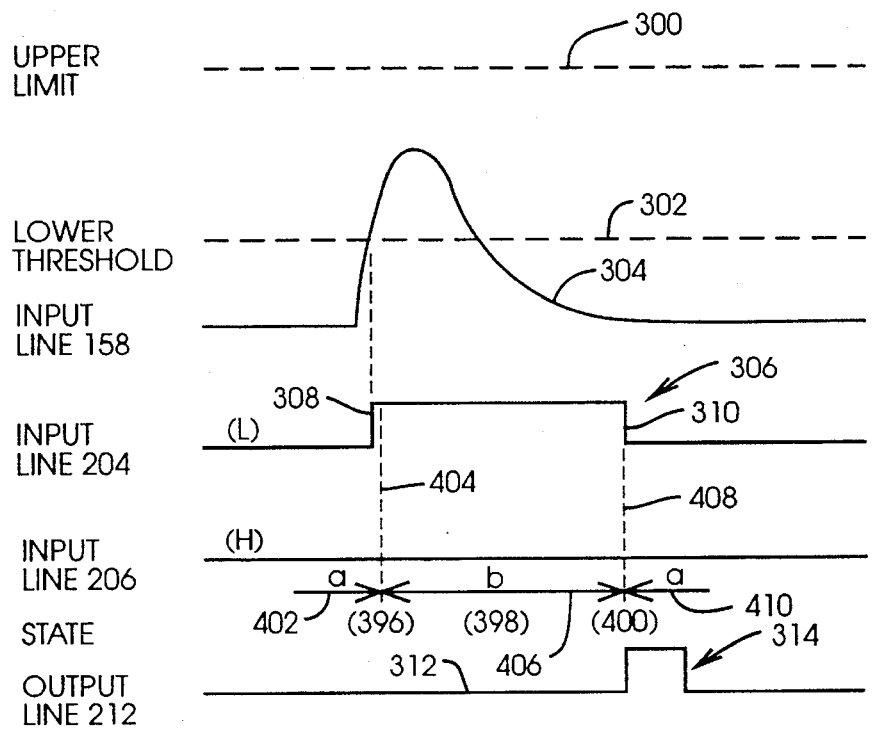
FIGS. 6A and 6B are curve and state combination drawings illustrating the operation of the networks of FIG. 5, and a discriminator circuit associated therewith.

Looking momentarily to FIG. 6A, the performance of the discriminator 210 is illustrated for a condition wherein a photon event is validated. In the figure, the upper limit level as established at comparator network 162 is represented at dashed line 300. Correspondingly, the level line for the lower threshold employed with network 164 is depicted as a level line 302. An input signal, for example as developed at line 158, is represented by the curve 304 as extending above lower threshold level line 302 but remaining below upper limit level line 300. Thus, the pulse represented by curve 304 is a valid one. The pulse generated by lower threshold network 164 at line 204 will develop a pulse of consistent width having a rising edge commencing as the curve 304 passes or encounters the lower threshold level represented at line 302. This condition will cause a commencement of the generation of a pulse of predetermined width at line 204 and such pulse width is represented generally at 306 having a rising edge 308 occurring as the curve 304 reaches or encounters the lower threshold level at level line 302. The following edge of pulse 306 is shown at 310 representing the fixed pulse output of monostable multivibrator 290. For this validating condition, as the transition represented by falling edge 310 occurs, a pulse of finite duration occurs at output line 212 as represented at curve 312 and pulse 314. This is a pulse which is counted, for example at counter network 214.

Figure 6B:
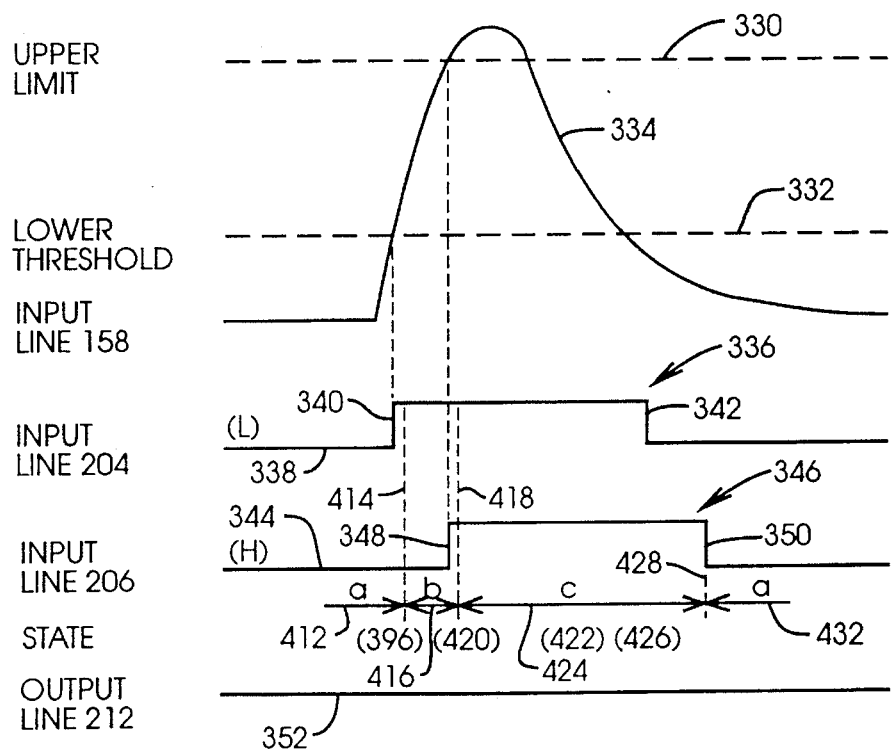

Now considering a condition wherein a signal representing an illegal event which not only passes the lower threshold, but also is of such magnitude as to pass the upper limit, reference is made additionally to FIG. 6B. Such a pulse may, for example, be occasioned as the result of a cosmic ray or the like. In the figure, the upper limit is represented by level line 330, while the corresponding lower threshold is represented by level line 332. An incoming signal at line 158 then may be represented by the signal defining curve 334 which not only passes the lower threshold represented at line 332, but also the upper limit as represented at line 330. The signal represented by curve 334, therefore, is one which is to be rejected by the discriminator network 210. As the signal magnitude initially encounters a lower threshold as represented at line 332, a lower threshold pulse will be generated as represented by the pulse 336 at curve 338. The rising edge of pulse 336 is shown at 340, while the falling edge thereof is represented at 342. Next, the signal represented by curve 334 will encounter and pass the upper limit level represented at line 330. Accordingly, a signal at input line 206, as represented at curve 344 will commence to define a pulse 346 at the rising edge 348 thereof. Pulse 346 is of the same width or duration as pulse 336 as defined by its falling edge 350 which is seen to occur subsequent to the falling edge 342 of pulse 336. The output of the discriminator circuit 210 at line 212 remains in a zero or no event condition as represented at curve 352.

Figure 7:
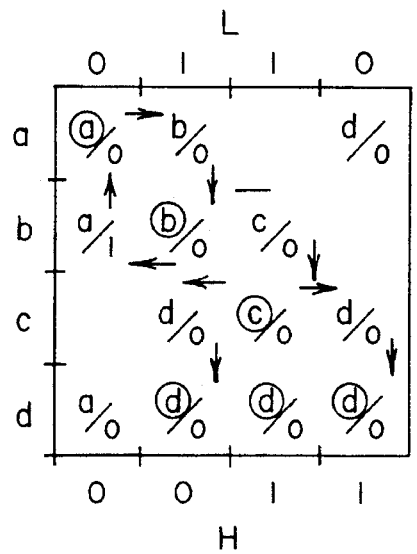
FIG. 7 is a semi-primitive flow chart employed in development of a discriminator circuit according to the invention.

The asynchronous fundamental mode circuit is developed initially with the observation that the present circuit will react to one of two inputs which may be designated as L or H, corresponding, for example, with respect to pulses 336 and 346 of FIG. 6B. Initially, a primitive flow chart is developed identifying conditions and potential states. Looking to FIG. 7, a semi-primitive flow chaff is represented for the instant circuit. Column headings in the chart are represented by the possible lower threshold, L, conditions 0110 and corresponding upper threshold conditions, H, of 0011. In assigning columns to the conditions, a Gray code form of arrangement is provided such that a change of only one variable at a time may occur. The rows of the chart of FIG. 7 are identified by state designations a–d. Additional such states normally would be added for a primitive flow chart which permits only one stable state per row. However, experience with the present system permits the utilization of a semi-primitive flow chart extending only to row d. In the chart, a state or row identification is represented by one of the row designators a–d, while a resultant output of either 0 or 1 is represented for each cell of the chart following a slash mark. Stable states are represented by an encircled row or state designator, and transitions are identified by small arrows. In this chart, stable state a, having a zero output, is seen present for the LH condition 00. An LH transition to 10 leads to the arbitrary and transient state b/0 which is driven downwardly to the b row and a stable b state condition with a continued 0 output. A subsequent LH transition to 00 results in leftward movement to a non-stable state a/1 with the noted unique one output which, as represented by the vertical arrow, returns forthwith or is driven to the stable state a/0. Should the H variable transition to a 1 with an LH condition 11, then an unstable c state with a 0 output (c/0) occurs and a driven transition to a stable c state with a 0 output as seen in row c. An LH transition to a 01 condition results in an unstable d state with 0 output which immediately is driven to the stable state d with a 0 output. Similarly, an LH transition to 10 from 11 results in the unstable state d with 0 output occurrence followed by a stable state d with 0 output as seen in row b. Note that there are three stable states in row d of the flow chart. Additionally seen in row d is the unstable state a with a/0 output and in row a is the unstable state d with an a/0 output.

Figure 8:
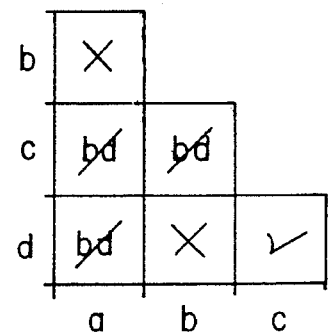
FIG. 8 is an implication table for analyzing the flow chart of FIG. 7.
Figure 9:
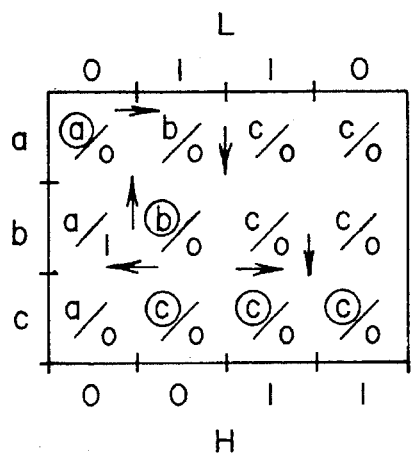
FIG. 9 is a reduced flow chart developed in connection with FIGS. 7 and 8.
Figure 10:
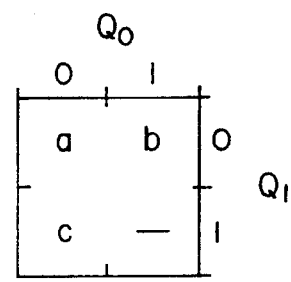
FIG. 10 is an assignment map.

Referring to FIG. 8, an implication table is illustrated for the semi-primitive flow chart of FIG. 7. This implication table is employed to determine whether there are rows of the semi-primitive flow chart which can be eliminated without affecting the required result. The evaluation looks to the presence of outputs which are the same for every column of two rows such that they become compatible. The implication table shows that no merger of rows is available except rows c and d. From this result, practitioners generally will develop a merger diagram, however, such diagram for the present development is trivial. Accordingly, as represented at FIG. 9, a reduced flow chart may be developed with the elimination of row d and insertion of the unstable state with 0 output c/0 at blank cells from FIG. 7. This diagram shows the reoccurrence of a stable state a with 0 output for the LH condition 00 and a corresponding stable state b for the LH variable condition 10. This leads to the unstable state a with a 1 output transitioning again to stable state a. Following the development of the reduced flow chart, it then becomes necessary to develop an assignment map wherein measurable variables are assigned to the arbitrary states a, b, and c. With the map, the variables, Q0 and Q1 can be defined, however, the choice of assignment of variables with the map is non-trivial. Generally, more than one assignment arrangement is contemplated with a reliance on experience of the designer. FIG. 10 shows an assignment for the variables Q0 and Q 1 with respect to states a, b, and c, the lower right quadrant of the map being represented as a "don't care", an assignment which itself may not be trivial. With the development of the assignment map of FIG. 10, recognition is made that there is a finite interval in the propagation of signals through any circuit. In this regard, looking to FIG. 11, the logic of such a circuit is represented at block 370. The signals L and H are introduced to this logic circuit 370 as represented at respective arrows 372 and 374. The result of application of variables LH to the logic circuit 370 develops corresponding output variables Q0 and Q1 as represented at respective arrows 376 and 378. Generally, a feedback may be implied of both Q0 and Q1 back to the input of logic 370. Thus, the feedback of output variable Q0 at line 376 is represented at feedback path line 380. The employment of logic circuitry necessarily implies a delay as represented by the delay block 382. While the delay may be short and in the nanosecond range, it is not 0 and is finite. Thus, the variable $q_0$ is represented as being that state which occurs prior to the transition to Q0. Similarly, the output arrow 378 carrying variable Q1 is shown having a feedback path 384 and delay block 386 to provide a variable $q_1$ occurring during the transition to variable Q1. The delays normally encountered in the logic of block 370 in the above discussion have been lumped into the blocks labeled "D" as at 382 and 386. These delays depend upon the actual implementation of the logic represented at block 370 and, as noted, are normally in the nanosecond range. In the actual circuit implementation discussed later, the delay blocks 382 and 386 do not exist.

Figure 12:
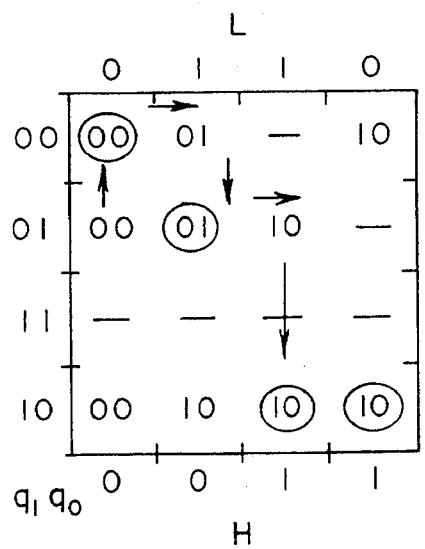
FIG. 12 is an excitation table developed with respect to FIGS. 9 and 10.
Figure 13:
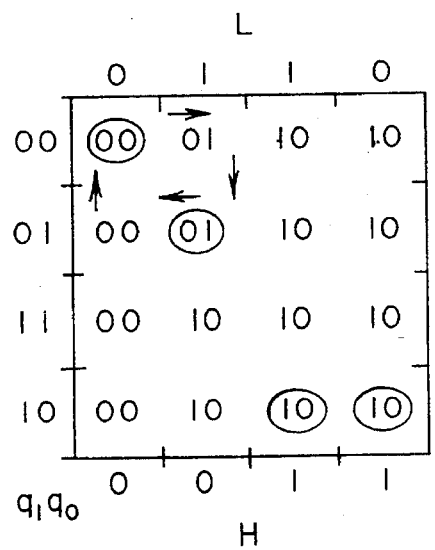
FIG. 13 is an excitation table representing a further development of the table of FIG. 12.
Figure 14:
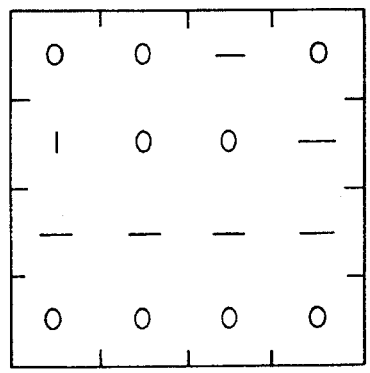
FIG. 14 is an output table developed with respect to FIG. 12.
Figure 15:
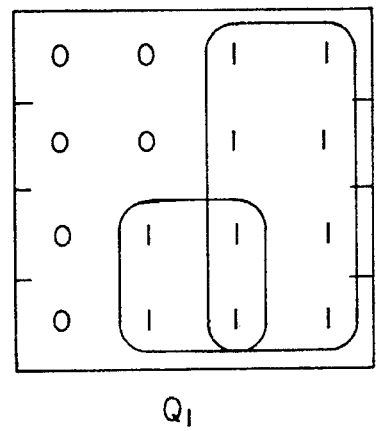
FIG. 15 is an output table with respect to the variable Q1.
Figure 16:
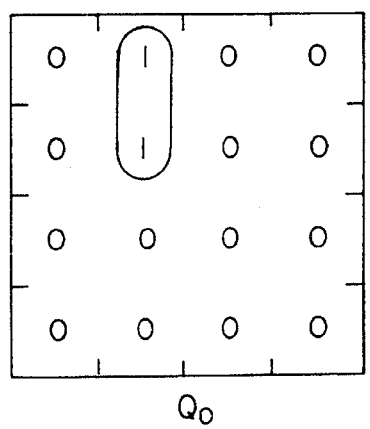
FIG. 16 is an output table developed with respect to the variable Q0.

From the assignment map of FIG. 10 and the reduced flow chart of FIG. 9, an excitation table as set forth in FIG. 12 initially may be developed. An excitation table presents the excitation state and output state as functions of the total state. Each column of the table of FIG. 12 is associated with a unique input state as labeled for LH and each row of the table corresponds to a unique secondary state $q_1$, $q_0$. As before, stable states are indicated by encircling the corresponding excitation state. The table of FIG. 12 further contains small dashes within cells which again represents the earlier-noted "don't care" condition. The states within the table are for the sequence Q1, Q0. It should be borne in mind that the variable $q_0$ is only equal to Q0 after the transition occurs, i.e. the earlier discussed delay. The delay of interest in the tables for the $q_1$, $q_0$ condition of 01 providing a 00 output for Q1, Q0 at the second row of the table in the first column. FIG. 13 shows the table of FIG. 12 with transient assignments located at the "don't care" position. These assignments are elected to avoid locking into one particular state and any other anomalies. This makes a resultant circuit predictable. Accordingly, by assigning outputs in the above manner, momentary changes in the output will be avoided when the circuit passes through unstable states. The information of FIG. 13 can be transferred to Karnaugh maps. In this regard, referring to FIG. 15, a variable Q1 is mapped. From this table, a Boolean logic equation may be developed as follows: Q1=H+L $q_1$. Similarly, in FIG. 16 the variable Q0 is mapped. The Boolean logic equation for this variable then becomes: Q0=L $\overline{Hq_1}$, while the output may be derived as the value $\overline{LH}$ $q_0$ $\overline{q_1}$. In the latter expression, the variable $q_0$ is a delayed variable. The output function will produce the desired output at the appropriate state transition, however, the duration of this output, without more, will be extremely short, e.g. 5 to 10 nanoseconds. To insure reliable actuation of the counting circuit 214, this output will be seen to be stretched by comparing a delay on Q0 as described later herein in conjunction with FIG. 18.

Figure 17:
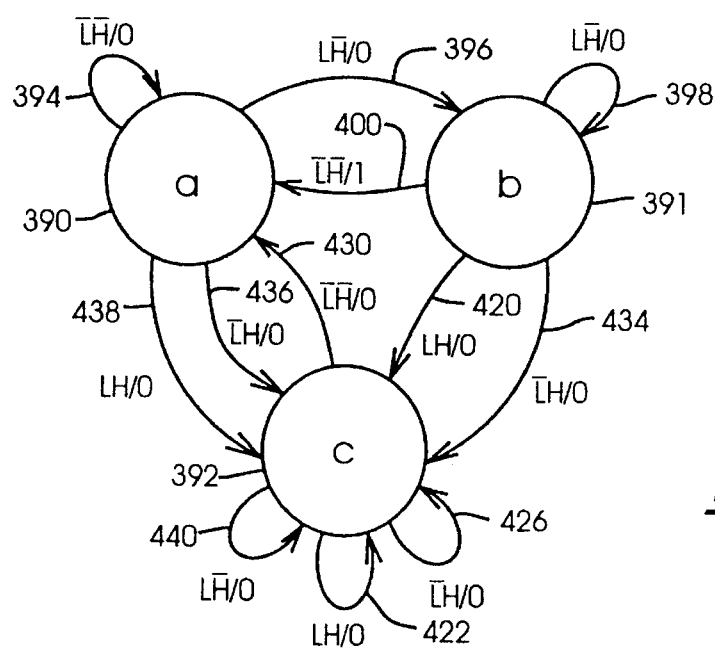
FIG. 17 is a state diagram describing the discriminator circuit of the invention.

The discriminator circuit with states a, b, and c also may be described in conjunction with a state diagram. Referring to FIG. 17, such a state diagram is presented with the noted states a–c being represented by respectively labeled circles 390–392. Resting state a at circle 390 is one wherein there is no pulse signal present from either of the comparator networks 162 or 164, i.e. an $\overline{L}$ $\overline{H}$/0 condition obtains. As represented at transitional loop 394, that condition provides for the retention of state a. However, should a pulse commence, for example having been derived at lower threshold network 164, then as represented by transition arc 396, a transition is made to state b represented at circle 391. The condition $\overline{L}$ $\overline{H}$/0 if continuing or recurring will cause the maintenance of state b as represented by the transition loop 398. However, if the pulse output from monostable multivibrator 290 is provided without the presence of a signal output from device 276, then a transition represented by transition arc 400 occurs with the corresponding output from the discriminator function of 1, i.e. a pulse. The condition then may be represented as $\overline{L}$ $\overline{H}$/1 as labeled upon the arc 400. The circuit then will have returned to stable state a as represented at circle 390 and an output transition to 0. Looking momentarily to FIG. 6A, the above state transitions may be observed. In the figure, a time line 402 represents the presence of state a until a point in time just shortly following the rising edge 308 of pulse 306. This is represented by state dividing line 404 below which the identification of transition arc 396 is provided in parenthesis. State b then ensues as shown at time line 406 and transitional loop identifying number 398. Stable state a reoccurs with the falling edge 310 of pulse 306 as represented at state dividing line 408 and time line 410. It is with this transition that the output pulse 314 is generated.

Returning to FIG. 6B, state transitions associated with an illegal pulse which exceed both the lower threshold and the upper limit may be demonstrated. In FIG. 6B, state a is seen to occur as represented at time line 412 until a point in time just following the creation of the rising edge 340 of pulse 36 as generated from comparator network 164. As represented by state dividing line 414 and transitional arc 396 shown in parenthesis below line 414, state b then ensues as represented at timeline 416. State b continues as represented at circle 391 and transitional loop 398 with the variable conditions L $\overline{H}$/0. Then, an output from upper limit network 162 will commence with the rising edge 348 of pulse 346. Shortly following the generation of rising edge 348, as represented at state dividing line 418, stable state c will ensue. In FIG. 17, a transition occurs for the condition LH/0 as represented at transition arc 420 and state c as represented at circle 392. Transition arc 420 is represented in FIG. 6B in parenthesis below state dividing line 418. Then, as represented by transition loop 422 in FIG. 17 and time line 424 in FIG. 6B, state c ensues. Pulses 342 and 346 are of the same width and, thus, the falling edge 342 of pulse 336 next will occur to develop the condition $\overline{L}$ H/0 represented in FIG. 17 as loop transition 426. That number is reproduced in parenthesis in FIG. 6B at the state c time line 424 beneath falling edge 342 of pulse 336. The logic level at curve 338 is now at a logic low while the logic level at curve 344 remains high as a continuum of pulse 346. Then, with the occurrence of the falling edge 350 of pulse 346, state c terminates as represented at state dividing line 428 and the condition is now $\overline{LH}$/0, a transition represented in FIG. 17 at transition arc 430. State a then ensues as represented at time line 432 in FIG. 6B. That figure further shows that during the coincidence of both pulses 336 and 346, the condition LH/0 will be present. This is represented in FIG. 17 at the loop transition 422.

The state diagram of FIG. 17 additionally shows other possible logic events and the results therefrom. For example, the presence of a condition $\overline{L}$ H/0 in connection with state b will result in the transition represented by transition arc 434, providing a transition to state c. Theft same condition when occurring during state a will result in a transition to state c as represented at transition arc 436. Similarly, a condition LH/0 occurring during state a will result in a transition to state c which is represented by transition arc 438. The implementation of the discriminator circuit may take a variety of forms depending upon the desire of the designer.

Figure 18B:
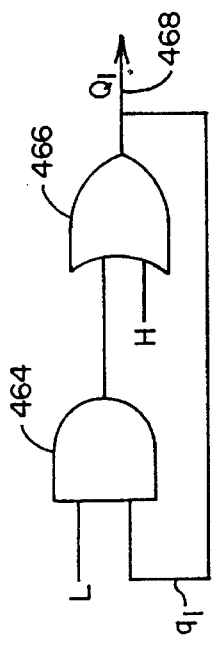
FIGS. 18a and 18B are implementation diagrams developed with respect to to FIGS. 14–16.
Figure 11:
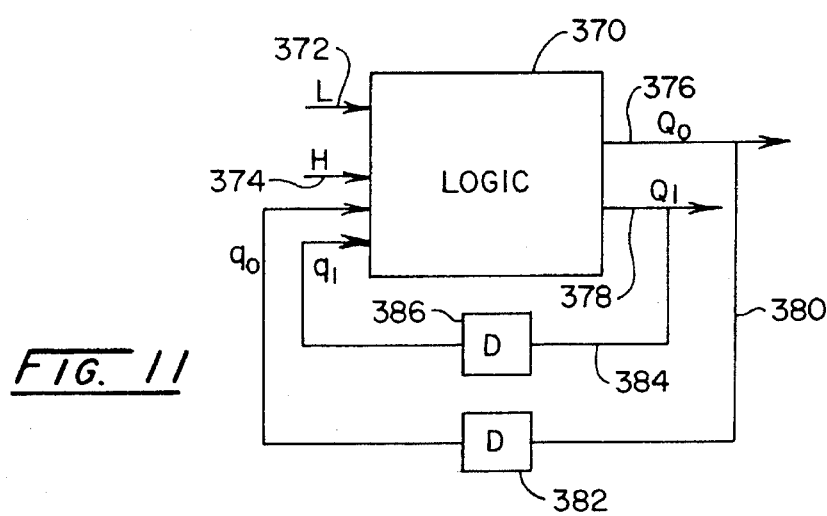
FIG. 11 is a fundamental mode circuit model for the discriminator circuit of the invention.
Figure 18A:
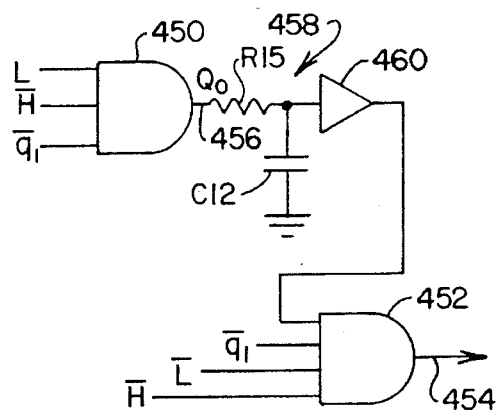

The above equations of circuit performance can be realized with appropriate logic devices. For example, looking to FIG. 18, the equation for "Output" and Q0 are combined, respectively, with logic devices 450 and 452 to provide a pulse output at line 454. Because the positive pulse generating output is involved with a transient, it is helpful to assert a delay on Q0 at the output of device 450, i.e. as represented at line 456. In this regard, an R-C delay network 458 is shown interposed with a representation for a pulse-shaping amplification stage 460. Network 458 is seen to be comprised of resistor R15 and capacitor C12. It may be observed that since the delay blocks labeled "D" in FIG. 11 are not real, the delayed variable $q_0$ is unavailable. It further may be noted that the point of insertion of the delay produced by resistor R15 and capacitor C12 of network 458 cannot affect the state transitions described previously. FIG. 18B shows a logic device implementation for Q1 as being implemented with logic devices 464 and 466 to provide Q1 at line 468. Preferably, however, the above equations can be programmed into an electronically programmable logic device (EPLD), for example a type EPM5130 marketed by Allera Corporation of San Jose, Calif.

Since certain changes may be made in the above described system and apparatus without departing from the scope of the invention herein involved, it is intended that all matter contained in the description thereof or shown in the accompanying drawings shall be interpreted as illustrative and not in a limiting sense.

I claim:

1. A system for detecting photon emissions, each occurring at an energy of interest within a range thereof, comprising:

a crystal detector assembly having an input confronting said photon emissions and responsive thereto to derive electrical parameter signals each having an amplitude corresponding with said energy of interest;

a first comparator network responsive to each said electrical parameter signal and having an output, L, when said signal exhibits a said amplitude of value above a threshold value;

a second comparator network responsive to each said electrical parameter signal and having an output, H, when said signal exhibits a said amplitude of value above an upper limit value;

an asynchronous, sequential, fundamental mode discriminator circuit responsive to said output, L, and said output, H, having three stable states a, b, and c, and having a no-event output condition when in a said stable state, said discriminator circuit transitioning from said state a to said state b upon the occurrence of said output, L, without the presence of said output, H, and transitioning from said state b to said state a to derive an event output upon the termination of said output, L, during state b, without the presence of said output, H; and control means responsive to each derived said event output for effecting an evaluation thereof.

2. The system of claim 1 in which said discriminator circuit is responsive when in said stable state, b, to said output L and said output H to transition with a no-event output condition to said stable state, c.

3. The system of claim 1 in which said discriminator circuit is responsive when in said stable state b to said output, L, in the absence of said output H to remain in said stable state b.

4. The system of claim 1 in which said discriminator circuit is responsive when in said stable state b to said output H in the absence of said output L to transition with a said no-event output condition to said stable state c.

5. The system of claim 1 in which said discriminator circuit is responsive when in said stable state c to the termination of said outputs H and L to transition with a said no-event output condition to said stable state a.

6. The system of claim 1 in which said discriminator circuit is responsive when in said stable state c to said output H in the absence of said output L to remain in said stable state c.

7. The system of claim 1 in which said discriminator circuit is responsive when in said stable state c to said outputs L and H to remain in said stable state c.

8. The system of claim 1 in which said discriminator circuit is responsive when in said stable state c to said output L in the absence of said output H to remain in said stable state c.

9. The system of claim 1 in which said discriminator circuit is responsive when in said stable state a to the absence of said outputs L and H to remain in said stable state a.

10. The system of claim 1 in which said discriminator circuit is responsive when in said stable state a to said output H in the absence of said output L to transition with a no-event output condition to said stable state c.

11. The system of claim 1 in which said discriminator circuit is responsive when in said stable state a to said outputs L and H to transition with a said no-event output to said stable state c.

12. The system of claim 1 in which said discriminator circuit is responsive when in said stable state b to said outputs L and H to transition with a said no-event output condition to said stable state c; and is responsive when in said stable state c to the termination of said outputs H and L to transition with a said no-event condition to said stable state a.

13. A system for detecting photon emissions, each occurring at an energy of interest within a range thereof, comprising:
- a crystal detector assembly having an input confronting said photon emissions and responsive thereto to derive electrical parameter signals each having an amplitude corresponding with said energy of interest;
- a first comparator network responsive to each said electrical parameter signal and having an output, L, of given pulse width when said signal exhibits a said amplitude of value above a threshold value;
- a second comparator network responsive to each said electrical parameter signal and having an output, H, of pulse width substantially equal to said given pulse width when said signal exhibits a said amplitude of value above an upper limit value;
- an asynchronous, sequential, fundamental mode discriminator circuit responsive to said output, L, and said output, H, having three stable states a, b, and c, and having an event output and a no-event output condition, and having said no-event output condition when in a said stable state, said discriminator circuit transitioning from said state a to said state b upon the occurrence of said output, L, without the presence of said output, H, responsive when in said stable state b to the occurrence of said output H in the presence of said output L to transition with a said no-event output condition to said stable state c, and responsive when in said stable state c to the termination of said outputs L and H to transition with a said no-event output condition to said stable state a; and
- control means responsive to each derived said event output for effecting an evaluation thereof.

14. The system of claim 13 in which said discriminator circuit is responsive to transition from said stable state b to said stable state a to derive a said event output upon the termination of said output L without the presence of said output H, during said stable state b.

15. The system of claim 14 in which said discriminator circuit is responsive when in said stable state b to said output, L, in the absence of said output H to remain in said stable state b.

16. The system of claim 14 in which said discriminator circuit is responsive when in said stable state a to said output H in the absence of said output L to transition with a no-event output condition to said stable state c.

17. The system of claim 14 in which said discriminator circuit is responsive when in said stable state a to said outputs L and H to transition with a said no-event output to said stable state c.

* * * * *